United States Patent
Bremer et al.

(10) Patent No.: US 6,366,795 B1
(45) Date of Patent: Apr. 2, 2002

(54) BIOMEDICAL ELECTRODE WITH VITAL SKIN PENETRATION

(75) Inventors: Roger E. Bremer, Fort Pierce, FL (US); Daniel T. Pogany, Cuyahoga Falls; John M. Questel, Silver Lake, both of OH (US)

(73) Assignee: Biosignal Partners, Mentor, OH (US)

( * ) Notice: Subject to any disclaimer, the term of this patent is extended or adjusted under 35 U.S.C. 154(b) by 0 days.

(21) Appl. No.: 09/305,849

(22) Filed: May 5, 1999

(51) Int. Cl.$^7$ .................................................. A61B 5/04
(52) U.S. Cl. ...................... 600/395; 600/387; 600/397; 607/152; 204/468
(58) Field of Search ................................. 600/372–391; 607/152; 209/205; 204/450, 456, 468–470; 516/98

(56) References Cited

U.S. PATENT DOCUMENTS

| | | |
|---|---|---|
| 3,580,254 A | 5/1971 | Stuart |
| 3,636,922 A | 1/1972 | Ketner |
| 3,826,245 A | 7/1974 | Funfstuck |
| 4,215,696 A | 8/1980 | Bremer et al. |
| 4,460,370 A | 7/1984 | Allison et al. |
| 4,526,176 A | 7/1985 | Bremer et al. |
| 4,693,711 A | 9/1987 | Bremer et al. |
| 4,699,146 A | * 10/1987 | Sieverding ................. 128/640 |
| 4,848,353 A | * 7/1989 | Engel ........................ 128/640 |
| 5,352,386 A | * 10/1994 | Rahman et al. ............. 252/548 |
| 5,779,632 A | * 7/1998 | Dietz et al. ................. 600/391 |
| 5,800,685 A | * 9/1998 | Perrault ...................... 600/391 |
| 5,821,280 A | * 10/1998 | Suda et al. ................... 522/84 |
| 5,985,990 A | * 11/1999 | Kantner et al. ............. 524/765 |

OTHER PUBLICATIONS

SNAPPY—A New Approach to Biosensor Systems; pp. 1–18.
AJIDEW—Ajinomot Co., Inc., Tokyo, Japan; pp. 5–16.
AROSET 1810–Z–52; Pressure Sensitive Adhesive; Ashland Chemical Company; Jun. 1986.

* cited by examiner

Primary Examiner—Linda C. M. Dvorak
Assistant Examiner—David M. Ruddy
(74) Attorney, Agent, or Firm—Fay, Sharpe, Fagan, Minnich & McKee, LLP

(57) ABSTRACT

An electrolyte (70) for use in a single-use biomedical electrode assembly (A, B, C, D) designed for receiving body-generated electrical signals at a patient's skin surface includes:

| Component | Range (%) |
|---|---|
| Skin penetration agent | 10–25 |
| Thickener | 0–10 |
| Alkali metal or alkaline earth metal chloride | 1–13 |
| Alkali metal or alkali earth metal nitrate | 1–13 |
| Surfactant | 0.001–5 |
| Soluble silver salt, as silver | 0–0.01 |
| Buffer | 0–10 |
| Water | Q.S. |

The skin penetration agent improves penetration of the outer, dead skin layers by the electrolyte, thereby improving pickup of minute electrical signals generated within the patient's body. A preferred skin penetration agent includes sodium 2-pyrrolidone-5 carboxylate at a concentration of 15–20% by weight of the electrolyte composition. Penetration of the composition is augmented by the hydraulic force of a snap-down housing (24) and by a skin adhesive (94) for effective sealing and adherence to the patient's skin.

21 Claims, 4 Drawing Sheets

BIOMEDICAL ELECTRODE WITH VITAL SKIN PENETRATION

BACKGROUND OF THE INVENTION

The present invention relates to biomedical electrodes, particularly an electrolyte formulation for use with a single use, disposable biomedical electrode, which provides improved skin penetration and conductivity, and will be described with particular reference thereto. It should be appreciated, however, that the invention is also applicable to a wide variety of biomedical electrodes.

Biomedical electrodes of various types are available for transferring current signals between the skin of a person and an external circuit. Electrodes used in electrocardiography (ECG) are classed as "monitoring" or "diagnostic." Monitoring electrodes are those which are used in demanding or lengthy applications, such as stress testing, critical care, heart monitoring, and the like. Diagnostic electrodes are generally used for less demanding applications and short term diagnoses.

In order to provide good electrode contact between an electrical terminal and the person's skin, it is customary to apply an electrolyte between the electrical terminal and the skin. The electrolyte may be absorbed in a support medium, such as a sponge, or located in a chamber which can be closed off by a porous membrane.

ECG electrodes fall into two general types, namely electrodes in the form of a flat patch unit, or electrodes comprising a pre-gelled electrolyte in a domed housing. Both types of electrode are generally passive, in that they lie passively on the skin surface waiting to pick up signals from within the body.

U.S. Pat. Nos. 4,216,969 and 4,693,711, to Bremer, et al. disclose examples of domed disposable biomedical electrodes for pressurized skin contact. The electrodes include a vaulted dome-like electrolyte-containing chamber or cavity which is closed at its open end by a highly flexible, conformable and hydrophobic microporous membrane. For storage, the membrane is covered with an adhesively secured protective film which is adapted to be stripped prior to adhesively securing the electrode to the skin of a patient. When downward pressure is applied to the vaulted housing, the housing is physically compressed and electrolyte within the chamber is pumped through the membrane into positive and low-electrical resistance contact with the skin surface of the patient. The housing is configured to maintain a positive, sustained pressure of the electrolyte against the skin surface, providing a low-impedance connection between the skin of the patient and the electrode terminal.

The signals which cardiologists and other diagnosticians seek to detect are sometimes very low. For example, signals generated by the heart are of the order of 0.005 volts. The outer layers of the epidermis, particularly the dead skin layer or stratum corneum, are poorly conducting. Typically, the skin surface impedance is around 54 kilo ohms, which provides a barrier to the reception of such minute signals by present types of electrolytes. The signal must traverse both the skin surface and the electrode before it is detected by the electrocardiographic instrument.

There remains a need for an electrolyte capable of penetrating the outer epidermal layers for improved signal conduction.

The present invention provides for a new and improved electrode system and electrolyte composition which overcome the above-referenced problems and others.

SUMMARY OF THE INVENTION

In accordance with one aspect of the present invention, an electrolyte composition for use in a biomedical electrode assembly is provided. The electrolyte composition includes an electrically conducting salt system and a salt of pyrrolidone carboxylic acid.

In accordance with another aspect of the present invention, an electrolyte composition for use in a biomedical electrode assembly is provided. The electrolyte comprises, by weight:

a) 1–14% of an electrically conducting salt system;

b) 10–25% of a skin penetration agent;

c) 0–10% of a thickener;

d) 0.001–5% of a surfactant;

e) 0–10% of a pH modifier; and, f) water.

In accordance with yet another aspect of the present invention, a single-use biomedical electrode assembly for receiving body-generated electrical signals at a skin surface of a subject is provided. The electrode assembly includes an inverted, deflectable, generally dish-shaped housing having a vaulted dome-like roof, a base, and an integrally formed, laterally extending annular flange at the base. The housing presents a downwardly directed opening bounded by an inward edge of the flange. A porous, fluid-permeable membrane covers the housing opening. The housing and the membrane define a chamber for an electrolyte. An electrolyte fills the chamber. The electrolyte includes an electrically conducting salt system and a skin penetration agent for increasing a penetration of the electrolyte through an outer layer of the subject's skin. The membrane is permeable to the electrolyte when a pressure is applied to the electrolyte. An electrically-conductive terminal is sealed to and extends through the roof of the housing and provides electrically-conductive communication between the exterior of the housing and the electrolyte within the chamber.

In accordance with yet another aspect of the present invention, a single-use biomedical electrode assembly for receiving body-generated electrical signals at a skin surface of a subject is provided. The electrode assembly includes a base layer of a first non-porous material and an intermediate layer of a second non-porous material. The intermediate layer defines an aperture and is sealed at a first surface to an inner surface of the base layer around the aperture to define a chamber. An electrolyte fills the chamber. The electrolyte includes an electrically conducting salt system and a skin penetration agent for increasing a penetration of the electrolyte through an outer layer of the subject's skin. An electrode material provides electrically-conductive communication between the exterior of the electrode assembly and the electrolyte within the chamber.

One advantage of the present invention resides in improved skin penetration and enhanced electrical conductivity of current signals while maintaining a desirable ionic and pH balance.

Another advantage of the present invention is that the electrolyte is suited for use in a low cost, disposable electrode, with extended shelf life.

Yet another advantage of the present invention is its applicability to a variety of measurements, including monitoring and stress testing, diagnostic electrocardiograms (ECG), and other applications.

A further advantage of the present invention is that the electrolyte functions effectively over a period of several days, and is suited to long term studies.

A yet further advantage of the present invention is that the skin preparation is reduced or eliminated.

A yet still further advantage of the present invention is the provision of an electrolyte with emollients for improved skin comfort.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangement of components and in various steps and arrangements of steps. The drawings are only for purposes of illustrating a preferred embodiment and are not to be construed as limiting the invention.

DETAILED DESCRIPTION OF THE PREFERRED EMBODIMENTS

An electrolyte composition for use with biomedical electrode assemblies includes an aqueous salt system for providing electrical conductivity and a skin penetrating agent. The composition, preferably, also includes a thickening agent and sources of silver and chloride ions. The composition may also include a pH modifier and a surfactant.

Suitable electrically conducting aqueous salt systems include one or more water-soluble salts. Suitable salts include alkali metal salts, alkaline earth metal salts, ammonium salts, and ionizable organic salts. The salt selected should, of course, be safe for use with the skin. Preferred salts include potassium chloride, potassium nitrate, sodium chloride, and calcium chloride. Potassium salts in general are preferred over sodium salts because the size to charge ratio of the molecules provides improved conductivity. A combination of potassium chloride and potassium nitrate is particularly preferred as the salt. A composition having a total salt concentration of 1–14% is preferred. Particularly preferred is a composition in which the salt comprises 1–13% potassium chloride and 1–13% potassium nitrate.

The skin penetration agent is one which improves the penetration of the electrolyte through the outer barrier layers of the epidermis of the skin, particularly the dead skin layer, or stratum corneum. Amino acid salts are preferred skin penetration agents. In particular, inorganic and organic salts of pyrrolidone carboxylic acids are preferred, such as sodium, potassium, calcium, magnesium salts. A particularly preferred skin penetration agent is sodium 2-pyrrolidone-5 carboxylate, which is sold under the trade name Ajidew N-50 by Ajnomoto Co., N.Y. as a 50% solution in water. The substance improves the effectiveness of the electrolyte in three ways. First, it softens and penetrates the skin; second, it acts as an electrical conductor; and third, it holds moisture and water in close contact with the skin. The composition preferably contains 10–25% sodium 2-pyrrolidone-5 carboxylate and more preferably 15–20% sodium 2-pyrrolidone-5 carboxylate. A particularly preferred concentration is around 18% by weight of the composition.

The thickening agent is included to provide a viscous aqueous mass, or gel. Preferably, the electrolyte is a thixotropic gel which is convertible to a flowable fluid-like composition upon physical disturbance, as through pressure applied to the gel. That is, the electrolyte is a semi-solid under dormant or storage conditions and is transformed into a liquid when the electrode is used. Suitable thixotropic thickening agents finding utility in the present composition include Cabosil, available from the Cabot Corporation, and Carbopol 934 NF, available from B.F. Goodrich, although the use of other water soluble or dispersible thickeners or resins, such as carboxymethylcellulose, polyvinyl alcohols, hydrophilic polyacrylic acids, and gums is also contemplated. The thickener is preferably at a concentration of 0–10% by weight of the composition. Where the thickener is Carbopol 934 NF, a preferred concentration in the composition is 2–6% by weight, most preferably, around 3.4%.

The concentration of the thickener, however, may vary, dependent on the electrode assembly in which the electrolyte composition is to be used. The thickener is added at a concentration sufficient to provide the required viscosity for the electrode assembly to be used. For some systems, the electrolyte should be of sufficient viscosity that it is retained by the electrode assembly until pressure is applied. However, for other systems, the viscosity is less important. The selected viscosity will also depend on the type of membrane employed, if a membrane is to be used. Generally, as the porosity of the membrane increases, the desired viscosity increases accordingly. It should be noted that the conductivity of the electrolyte tends to decrease with increasing viscosity and thus the selected viscosity is preferably close to the minimum acceptable for the system.

The electrolyte composition preferably includes a surfactant or wetting agent for improving electrical contact between the electrolyte and the skin surface. Suitable surfactants include anionic, cationic, and non-ionic surfactants. A preferred anionic surfactant is Igepal CO 630. Other preferred surfactants include disodium ethoxylated alcohol half esters of sulfosuccinic acid obtainable under the trade name Aerosol 102 from American Cyanamid Co, Wayne, N.J., and sodium 2-ethyl 1-hexyl sulfate, available under the trade name Carsonol SHS from Carson Chemicals, Inc., Long Beach, Calif. A preferred surfactant concentration is 0.001–5% by weight of the composition, with a particularly preferred concentration of 0.01–0.5% by weight.

When the electrolyte is to be used with an electrode assembly which incorporates a silver-silver chloride electrode material, the electrolyte preferably includes sources of silver and chloride ions. The excess of silver and chloride ions in the electrolyte inhibit the dissolution of the silver chloride film of the electrode material. Otherwise, the silver chloride of the electrode material tends to interact with sodium chloride in the electrolyte over time and the sodium chloride then corrodes or forms a complex with the metal of the electrode. By saturating the electrolyte with silver chloride, the breakdown of the silver-silver chloride layer is minimized. Suitable sources of these ions include potassium chloride and silver nitrate, although other soluble sources of these ions are also contemplated. Preferably, the composition includes 0–0.01% by weight silver, in the form of a soluble silver salt, more preferably 0.001–0.003% silver.

The electrolyte composition preferably includes a pH modifier to adjust the composition to a pH suitable for skin contact. The pH modifier can be a true buffer, which maintains the pH of the electrolyte during use, or simply a pH adjuster, which brings the initial pH of the electrolyte into a desired range. The pH of the electrolyte composition is preferably in the range of pH 6.5 to pH 7.75 with a preferred pH of around neutral (pH 7). A particular preferred pH modifier is potassium hydroxide. This is added in sufficient quantity to bring the pH of the electrolyte composition into the desired range. The optimum pH of the composition may also be dependent on the selected thickener. For example, Carbopol thickener is only an effective thickener when the pH is neutral or slightly alkaline. In such circumstances a concentration of around 0–10% by weight potassium hydroxide, ore preferably 4–10% potassium hydroxide, brings the pH of the composition to neutral or slightly above neutral. For other thickeners, the optimum pH range may be modified to accommodate the thickening properties of the thickeners.

The electrolyte composition includes water to bring the concentration of salts to the desired concentrations and for the desired thickness to be obtained. The water is preferably deionized, although other forms of relatively pure water are also contemplated.

A preferred formulation of the electrolyte composition includes:

| Component | Range (Weight %) |
|---|---|
| Skin penetration agent | 10–25 |
| Thickener | 0–10 |
| Alkali metal or alkaline earth metal chloride | 1–13 |
| Alkali metal or alkali earth metal nitrate | 1–13 |
| Surfactant | 0.001–5 |
| Soluble silver salt, as silver | 0–0.01 |
| pH Modifier | 0–10 |
| Water | Q.S. |

Preferably, the combined concentration of chloride and nitrate salts is about 14% or less. A particularly preferred formulation is as follows:

| Component | Range (Weight %) |
|---|---|
| Sodium 2-Pyrrolidone-5 Carboxylate | 15–20 |
| Thickener | 2–6 |
| Potassium chloride | 2–12 |
| Potassium nitrate | 2–12 |
| Surfactant | 0.01–0.5 |
| Silver nitrate solution, 0.025N | 0.2–1 |
| 40% KOH in water | 4–10 |
| Deionized water | Q.S. |

Figure 1:
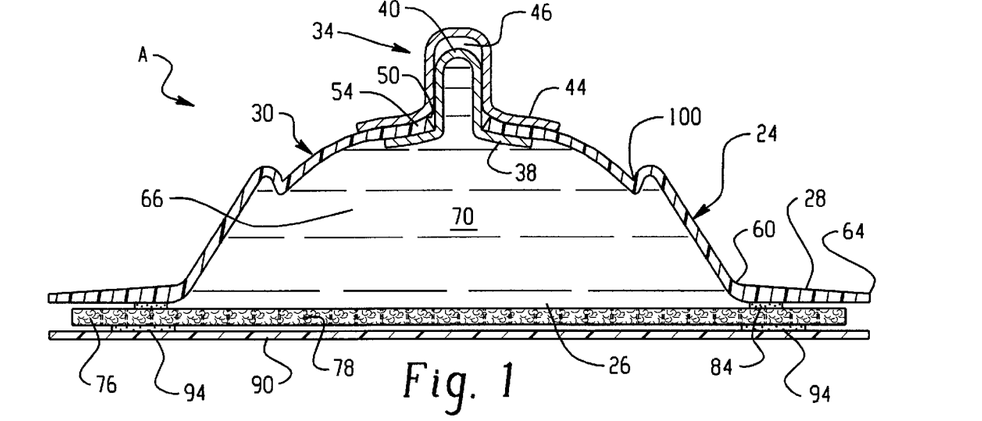
FIG. 1 is a side sectional view of a first embodiment of an electrode assembly prior to attachment to a body surface, such as the skin of a patient, according to the present invention.
Figure 2:
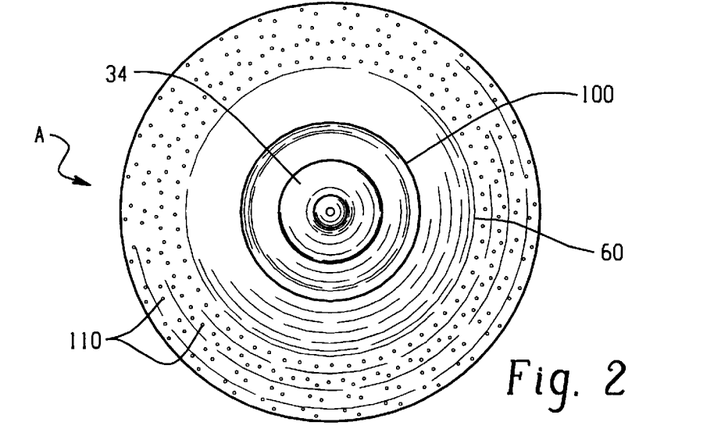
FIG. 2 is a top view of the electrode assembly of FIG. 1.
Figure 3:
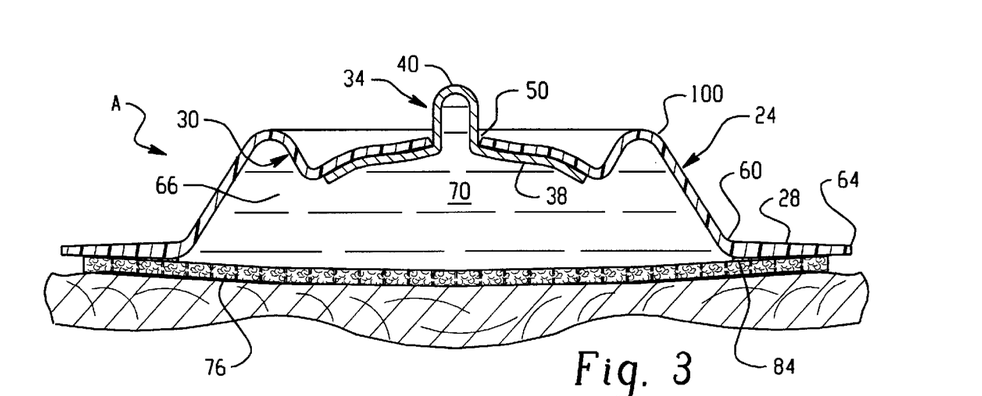
FIG. 3 is a side sectional view of the electrode assembly of FIG. 1 showing the configuration of the electrode assembly after the housing has been deformed to establish pressure on the electrolyte and contact of the electrolyte with the body surface of the patient.

With reference to FIGS. 1 to 3, a first preferred embodiment of an electrode assembly A incorporating the electrolyte composition is shown. The electrode assembly comprises an inverted, generally dish-shaped, plastic housing 24 with a downwardly directed lower opening 26 bounded by an annular laterally extending flange or rim 28. The housing has a vaulted dome-like roof 30, at the apex or center of which a terminal 34 is sealed to extend through the roof to provide an electrically conductive path between the exterior of the housing and its interior. Preferably, the terminal is molded in plastic and coated with silver/silver chloride, although other terminal compositions, such as coated brass, are also contemplated.

As best shown in FIG. 1, the terminal 34, constitutes a male snap fastener assembly consisting of a lower washer like disk 38 with a central, integrally formed upwardly extending stud 40. Optionally, as shown in FIG. 1, the terminal further includes a surmounting flanged conductive cap 44 formed with an upwardly projecting, downwardly opening stud receiving socket 46. To secure the terminal 34 to the roof 30 of the housing 24, the stud 40 of the lower component 38 is inserted upwardly to extend through an upper opening 50 at the apex of the roof 30 of the housing 24 and into the cooperating socket 46 of the cap 44. The two parts 38 and 44 are then forcibly pressed or crimped together to establish a mechanical interlock and to form a fluid-tight seal with the interposed plastic housing 24.

Alternatively, as shown in FIG. 3, the stud receiving socket may be omitted and the stud 40 simply inserted through the upper opening 50, which is sized to sealingly grip the stud.

With particular reference to FIGS. 1 and 3, the effectiveness of the seal between the roof 30 of the housing 24 and of the terminal 34 is optionally ensured by forming the upper extremity of the plastic housing with an integral, somewhat thickened, ring-like annular bead 54. The bead 54 is embraced on its opposed lower and upper surfaces by the annular flanges of disk and cap 38 and 44 of the snap fastener assembly 34, the bead 54 delineating a mechanically strengthened, compressible zone.

The integral annular flange 28 at the base of the housing is formed with a transverse thickness gradient which tapers from a greater thickness at its inner radial origin 60, adjacent its juncture with the vaulted housing wall, to a lesser thickness at its outer marginal periphery 64. This provides physical strength, rigidity, and stability in conjunction with enhanced conformability of the flange 28 to a body surface (not shown) of the patient, to which the flange 28 is to be ultimately adhesively secured. A chamber or cavity 66, within the domed housing is filled with an electrolyte 70, of the composition described herein. The electrolyte maintains electrical continuity between the skin surface to which the electrode assembly is secured and the terminal 34. The chamber 66 is preferably completely filled with the electrolyte.

The lower opening 26 in the electrode housing 24 is bridged by a porous membrane 76, preferably a microporous membrane. Openings 78 in the membrane 76 are exceedingly small, but large enough to permit fluid passage therethrough. A preferred membrane is a non-woven, spunbonded or spunlace material, such as Chicopee, although other woven and non-woven materials, such as CELGARD, are also contemplated. By control of surface tension and viscosity of the electrolyte, the ability to pass through the membrane is controlled. Adding a surfactant to the electrolyte permits a balance of forces inducing proper penetration and facilitates this passage.

The membrane 76 may be secured to the housing 24 in various ways. In a preferred embodiment, the membrane 76 is welded ultrasonically to provide a ring seal at a junction 84 of the housing wall with the horizontally extending flange 28. The junction of the flange 28 with the housing 24 is preferably microconvoluted or knurled, a configuration which facilitates ultrasonic bonding of the membrane 76 to flange 28 and ensures a positive, fluid-tight seal.

An alternate configuration is to replace the continuous flange 28 with a separate flange made of either a woven, non-woven, or film material of the same horizontal dimensions and simultaneously bonding the same to the dome portion of the electrode assembly at the junction 84, with a ring seal, when the membrane 76 is bonded to the housing 24 at junction 84; or to continue the membrane 76 beyond the junction 84 and use the membrane as the flange.

To prevent escape of fluid from the cavity 66 through the membrane 76 prior to use, the electrolyte is sufficiently thick that it does not seep through the pores of the membrane. A peelable film 90 is secured to the lower surface of the surrounding annular flange by an interposed, pressure-sensitive adhesive 94. The same adhesive which is exposed upon stripping of the protective film 90 also is used to anchor the electrode assembly A firmly in place on the skin surface of the patient or subject. Preferably, the adhesive 94 is applied in an annulus so that it does not obstruct passage of the electrolyte through the portion of the membrane which covers the lower opening 26. The adhesive used is preferably of a liquid compatible, emulsified type because the electrolyte 70 can be in either liquid or gel form. A preferred, pressure sensitive adhesive includes Aroset 1810 Z-52, available from Ashland Chemicals. This adhesive was shown to have good adhesion to the skin and resisted leakage of the electrolyte over an extended period.

The configuration of the cavity 66 beneath the housing 24 and above the membrane 76 is changed when the housing is depressed, the configuration being capable of assuming two stable states. With particular reference to FIGS. 1 and 3, which show the electrode assembly in two different positions, as assembled, and prior to actual use of the electrode assembly, the housing 24 is initially vaulted upwardly as shown in FIG. 1. The housing wall is formed with an offset band or inflection at its circumference to provide a ring-like transformation zone 100 which extends inwardly about the housing. The zone generally parallels a plane defined by the porous membrane 76. This transformation zone 100 functions as a mechanical discontinuity or toggle joint condition in the housing wall.

To operate the electrode assembly, the release film 90 is removed and the electrode assembly adhesively secured to a skin surface of a subject. A downward pressure, for example, finger pressure or that of the connector to a monitoring instrument, is applied to the vaulted roof of the housing at the center terminal 34. This causes the dome-like roof of the housing to be displaced downwardly and snap into the stable position shown in FIG. 4. The flexing zone 100 is then located at the upper edge of the now toroidal housing. This action initially distends the porous membrane. The distended membrane with its resiliency maintains continuous pressure on the electrolyte providing a pressure driving-force which assists electrolyte flow through its pores. The mechanical shift of the housing wall is somewhat analogous to a toggle phenomenon, since the depressed position of the roof of the housing constitutes a new stable orientation, and pressure within the cavity is maintained as a continuing state.

Optionally, the electrolyte is separated from the metal contact during storage. The electrolyte may be contained within a small capsule and placed into the cavity 66 before application the membrane 76. The capsule has a frangible or easily breakable skin. One or more of the components of the electrolyte may be contained inside the capsule. The capsule is ruptured when the housing is depressed. Alternatively, a membrane can separate the cavity into two compartments. To assist breakage, the membrane is preferably scored or grooved to form break or score lines and may include additives such as glass fibers, mica, talc, mineral fillers or other materials to assist rupturing of the membrane.

For long-term studies, the extending flange or rim 28 of the housing 24, which is made of plastic, is optionally perforated as seen at 110 to provide skin breathing holes, similar to perforations in plastic adhesive strips of small, self-holding bandages. This inhibits anaerobic bacterial build-up and together with included anti-bacterial material, such as parabens, provides a more sterile environment.

The electrode assembly thus described is an active, rather than a passive electrode, in that the proteolytic type electrolyte penetrates the stratum corneum, reaching into the more signal-rich dermis area of the skin, thereby overcoming the heavy impedance of the dead skin layer. Penetration is enhanced by the hydraulic force exerted by the snap down housing as the electrode is applied to the skin. The electrode assembly is suited to low-cost construction and may be of small size, preferably 2–3 cm in diameter, or less.

Figure 4:
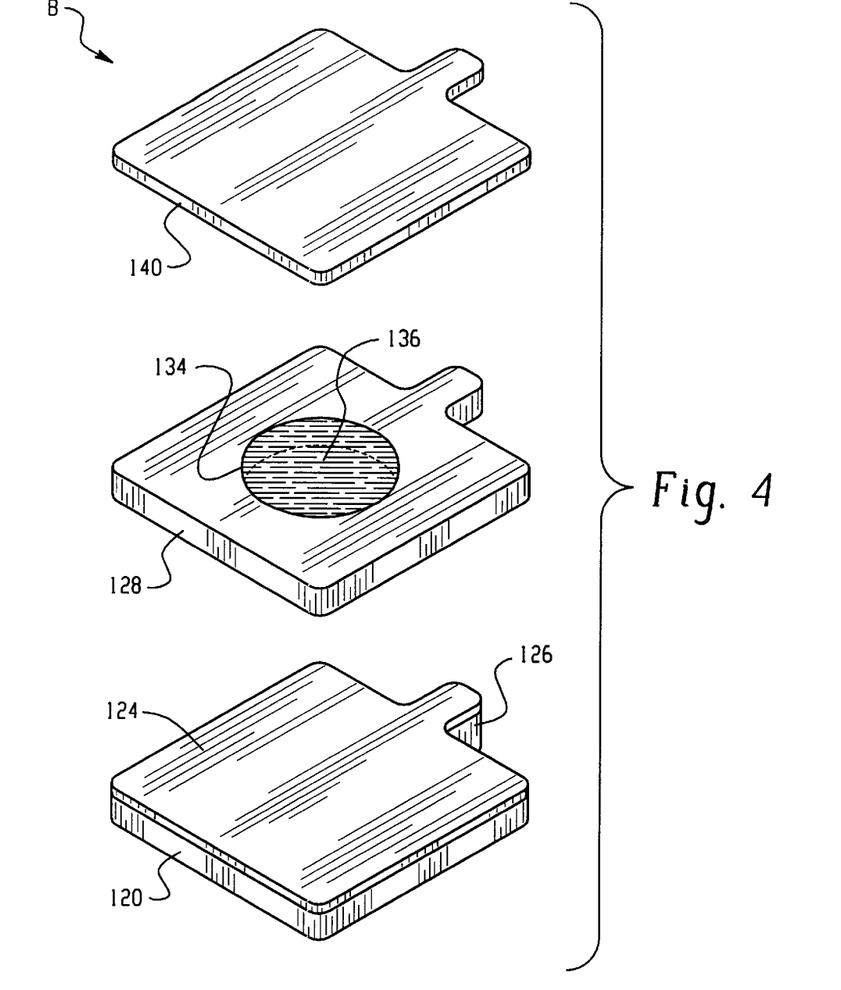
FIG. 4 is a perspective view of a low cost second embodiment of an electrode assembly according to the present invention.
Figure 5:
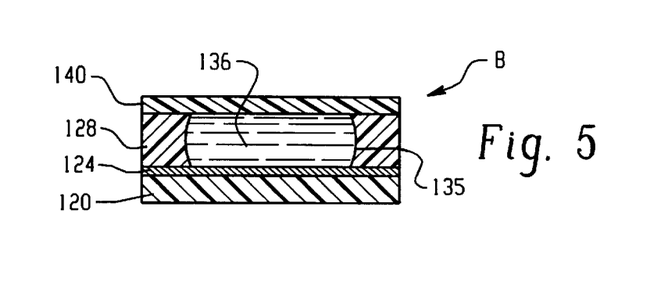
FIG. 5 is a side sectional view of the electrode assembly of FIG. 4.

With reference to FIGS. 4 and 5 an alternative embodiment of an electrode assembly B is shown. The electrode assembly includes a base layer 120, formed from a film of a non-porous material, such as Mylar. An inner surface of the base layer is coated with an electrode material 124, such as a silver/silver chloride ink, to form an electrode. The electrode material covers at least a central region of the base layer and extends to a protruding terminal portion 126, for connecting the electrode assembly to diagostic instrumentation, such as an EKG machine.

An intermediate layer 128 of a non porous material, such as pressure sensitive adhesive, defines a central aperture 134. The base layer is adhered around a peripheral edge to a lower surface of the intermediate layer, in an annulus around the aperture, to define a shallow chamber or well 135 within the aperture. An electrolyte gel 136, of the type described herein, fills the aperture well and contacts the conducting material at the base of the well. A release layer 140, formed from a non-porous material, such as polyvinyl chloride, is sealed to the intermediated layer, around the aperture. A strippable adhesive of the type previously described, which also serves to adhere the electrode assembly to the person's skin is preferred. The release layer 140 is removed from the electrode assembly prior to placing the electrode assembly on the skin of a patient. The electrolyte gel is preferably of a sufficient viscosity that it is retained between the skin and the barrier layer without excessive leakage. Alternatively, a microporous membrane (not shown) covers the electrolyte gel and the intermediate layer 128. The membrane is preferably formed from a non-woven material, such as Chicopee. The membrane is adhered to the intermediate layer with a suitable adhesive, as previously described.

Figure 6A:
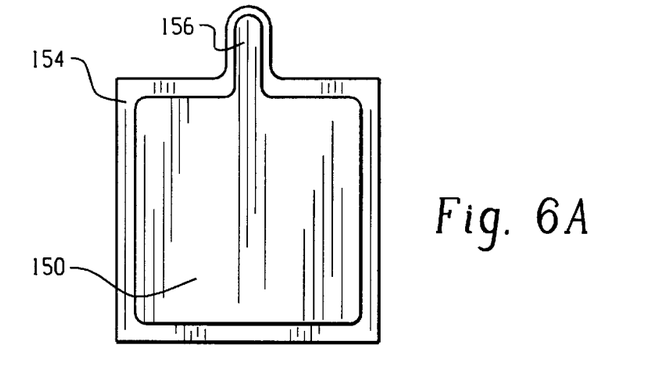
FIG. 6A is a top view of a base layer of a third embodiment of an electrode assembly according to the present invention.
Figure 6B:
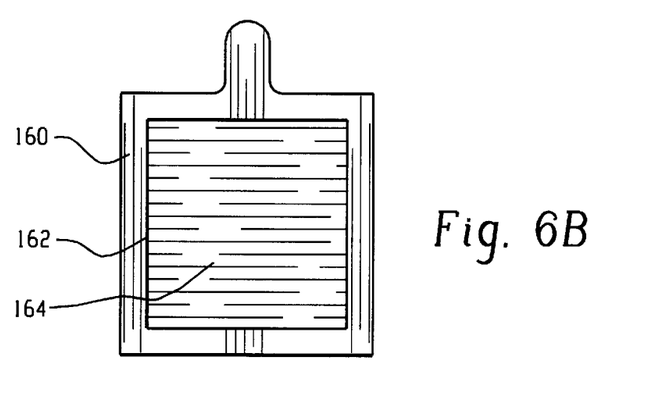
FIG. 6B is a top view of an intermediate layer for the embodiment of FIG. 6A.
Figure 6C:
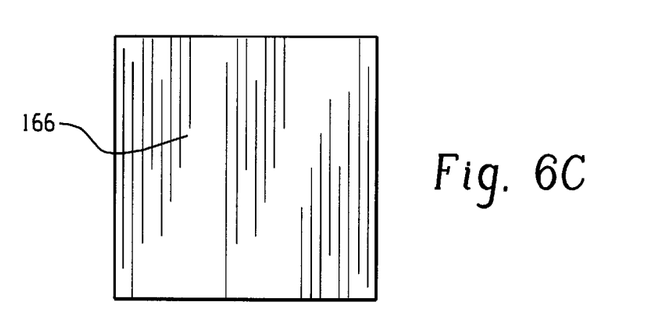
FIG. 6C is a top view of a release film for the embodiment of FIG. 6A.
Figure 7:
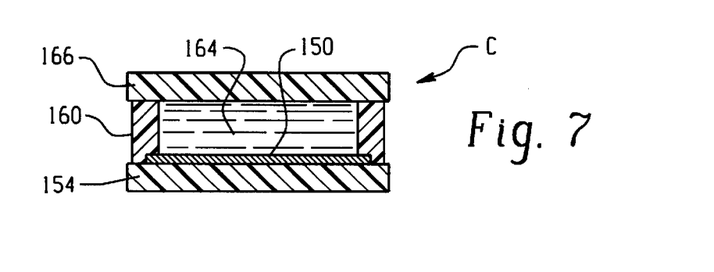
FIG. 7 is a side sectional view of the third embodiment of the electrode assembly.

With reference to FIGS. 6 and 7, a third embodiment of an electrode assembly C is shown. The electrode assembly is similar to that of the previous embodiment, except in that an electrode layer 150 covers only the central region of an inner side of a base layer 154 and a terminal portion 156. An intermediate layer 160 includes a central aperture 162. The intermediate layer and base layer are sealed together as before to define a shallow well within the aperture which is filled with an electrode material 164 of the present composition. As shown in FIGS. 6A and 6B, the electrode and the well are generally rectangular, although other configurations are also contemplated. A release layer 166, of the type previously described, is adhered to a periphery of an upper surface of the intermediate layer, around the aperture 162.

Figure 8A:
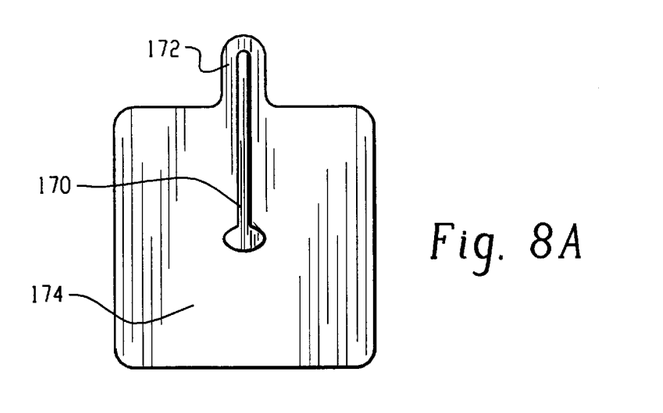
FIG. 8A is a top view of a base layer of a fourth embodiment of an electrode assembly according to the present invention.
Figure 8B:
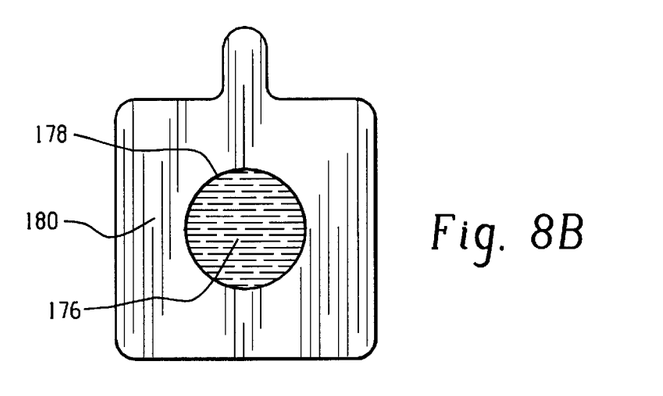
FIG. 8B is a top view of an intermediate layer for the embodiment of FIG. 8A.
Figure 8C:
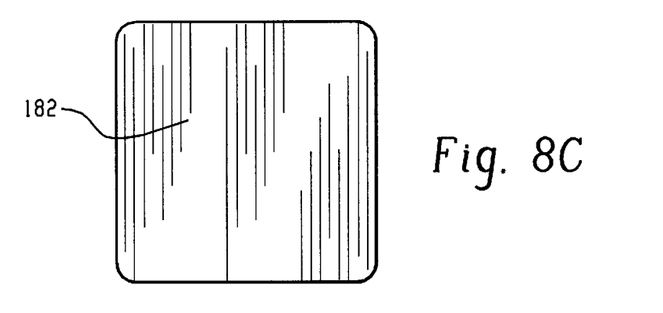
FIG. 8C is a top view of a release film for the embodiment of FIG. 8A.
Figure 9:
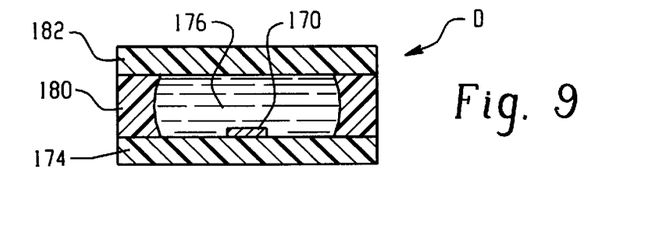
FIG. 9 is a side sectional view of the fourth embodiment of the electrode assembly.

With reference to FIGS. 8 and 9, a fourth embodiment of an electrode assembly D is shown. In this embodiment, a narrow strip of an electrode material 170 extends from a terminal portion 172 to a central region of the inner surface of a base layer 174. The electrode contacts an electrolyte gel 176 received in a central aperture 178 in an intermediate layer 180. A release layer 182 completes the electrode assembly, as before.

In an alternative embodiment of FIGS. 4–9, the electrolyte and adhesive are combined and applied together to the base layer.

While not intending to limit the invention, the following examples are illustrative of the electrolyte composition the copolymers of the present invention, their properties, and electrode assemblies in which they can be used.

EXAMPLE 1

An electrolyte was prepared according to the following formulation:

| Component | Weight | Percent |
|---|---|---|
| Sodium 2-pyrrolidone-5 carboxylate | 89.0 g | 17.7 |
| Carbopol 934 NF | 17.0 g | 3.4 |
| Potassium chloride | 26.0 g | 5.2 |
| Potassium nitrate | 35.0 g | 6.96 |
| Igepal CO 630 | 0.1 g | 0.02 |
| Silver nitrate solution, 0.025N | 2.0 g | 0.4 |
| 40% KOH in water | 35.0 g | 6.96 |
| Deionized water | 299.0 g | Q.S. |

The electrolyte was employed in the cavity of 66 of an electrode assembly A constructed according to the first embodiment, with a plastic terminal coated with silver/silver chloride.

The electrode assembly passed accelerated aging tests for shelf life and in use.

EXAMPLE 2

The operation of the present electrode assembly with the formulation of Example 1 was compared with three conventional electrodes using conventional electrolytes. Results for the three conventional electrode systems were averaged, as follows:

| Characteristic | Conventional Electrodes (Average of 3 types) | Electrode Assembly with Electrolyte of Present Composition |
|---|---|---|
| Critical Impedance | 165 ohm | 16 ohm |
| Defibrillation | 9.6 mV | 1.6 mV |
| Recovery after defibrillation | 110 ohm | 15 ohm |

As shown above, an electrode assembly using the current electrolyte gel outperformed conventional electrode systems.

Tests were also carried out using the present electrode assembly both with conventional passive electrode gels and with the electrolyte gel of the Example 1. Test results showed that the electrode assembly with the present electrolyte gel had one third of the impedance of the electrode assembly when used with conventional gels.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A biomedical electrode assembly comprising:
   an electrode body including an upper portion that defines a well and a peripheral lower surface;
   an electrode extending into the well;
   an electrolyte filling the well, the electrolyte including:
   a) an electrically conducting salt system, and
   b) a salt of pyrrolidone carboxylic acid which includes sodium 2-pyrrolidone-5 carboxylate at a concentration of 10–25% by weight of the composition; and,
   a pressure sensitive adhesive along the peripheral lower surface.

2. An electrolyte composition for use in a biomedical electrode assembly comprising, by weight:
   a) 2–12% of an electrically conducting salt system;
   b) 10–25% of a skin penetration agent, the skin penetration agent including an inorganic or organic salt of 2-pyrrolidone-5 carboxylic acid at a concentration of 15–20% of the composition;
   c) 2–6% of a thickener;
   d) 0.01–0.5% of a surfactant;
   e) 0–10% of a pH modifier, the pH modifier including potassium hydroxide at a concentration of 4–10% of the composition; and,
   f) deionized water.

3. The electrolyte composition of claim 2, wherein:
   the electrically conducting salt system comprises a salt from the group consisting of chlorides and nitrates of sodium, potassium, and calcium, and combinations thereof.

4. A biomedical electrode assembly comprising:
   an electrode body including an upper portion that defines a well and a peripheral lower surface;
   an electrode extending into the well;
   an electrolyte filling the well, the electrolyte including:
   a) an electrically conducting salt system, the salt system including potassium nitrate at a concentration of 1–13% by weight of the composition, and
   b) a salt of pyrrolidone carboxylic acid; and,
   a pressure sensitive adhesive along the peripheral lower surface.

5. The biomedical electrode assembly of claim 4, wherein the salt of pyrrolidone carboxylic acid is elected from the group consisting of sodium, potassium, calcium, and magnesium salts of pyrrolidone carboxylic acid.

6. The biomedical electrode assembly of claim 4, wherein the salt of pyrrolidone carboxylic acid includes only one pyrrolidone carboxylate monomer.

7. An electrolyte composition for use in a biomedical electrode assembly comprising:
   a) an electrically conducting salt system; and,
   b) a salt of 2-pyrrolidone-5 carboxylic acid which includes sodium 2-pyrrolidone-5 carboxylate at a concentration of 10–25% by weight of the composition.

8. The electrolyte composition of claim 7, wherein the sodium 2-pyrrolidone-5 carboxylate concentration is 15–20% by weight of the composition.

9. An electrolyte composition for use in a biomedical electrode assembly comprising:
   a) an electrically conducting salt system, the salt system including potassium nitrate at a concentration of 1–13% by weight of the composition; and
   b) a salt of pyrrolidone carboxylic acid.

10. The electrolyte composition of claim 1, wherein the salt system includes potassium chloride at a concentration of 1–13% by weight of the composition.

11. The electrolyte composition of claim 1, wherein the salt system includes potassium chloride and potassium nitrate at a total concentration of 1–14% by weight of the composition.

12. The electrolyte composition of claim 9, further comprising a thickener.

13. An electrolyte composition for use in a biomedical electrode assembly comprising:
   a) an electrically conducting salt system:
   b) an inorganic salt of Pyrrolidone carboxylic acid; and
   c) a thicker which is present in a quantity such that the electrolyte is a semi-solid that liquefies under pressure.

14. The electrolyte composition of claim 13, wherein the salt system includes an inorganic salt selected from the group consisting of alkali and alkaline earth metal chlorides and nitrates, and combinations thereof.

15. The electrolyte composition claim 13, further including a surfactant.

16. The electrolyte composition of claim 15, wherein the surfactant is an anionic surfactant at a concentration of 0.001–5% by weight of the composition.

17. The electrolyte composition of claim 16, wherein the anionic surfactant concentration is 0.01–0.5% by weight of the composition.

18. The electrolyte composition of claim 13, further comprising a pH modifier for adjusting the pH of the composition to about neutral.

19. The electrolyte composition of claim 13, further comprising a source of silver chloride.

20. The electrolyte composition of claim 19, wherein the source of silver chloride includes a soluble silver salt and a soluble chloride.

21. The electrolyte composition of claim 13, wherein the inorganic salt of pyrrolidone carboxylic acid is selected from the group consisting of sodium, potassium, calcium, magnesium salts of pyrrolidone carboxylic acid.

* * * * *